United States Patent
Kay

(10) Patent No.: US 8,725,538 B2
(45) Date of Patent: *May 13, 2014

(54) AUTOMATED PROCESSING OF ELECTRONIC MEDICAL DATA FOR INSURANCE AND DISABILITY DETERMINATIONS

(75) Inventor: Lay K. Kay, Pasadena, CA (US)

(73) Assignee: QTC Management, Inc., Diamond Bar, CA (US)

( * ) Notice: Subject to any disclaimer, the term of this patent is extended or adjusted under 35 U.S.C. 154(b) by 185 days.

This patent is subject to a terminal disclaimer.

(21) Appl. No.: 12/940,837

(22) Filed: Nov. 5, 2010

(65) Prior Publication Data

US 2011/0054947 A1     Mar. 3, 2011

Related U.S. Application Data

(63) Continuation of application No. 12/192,043, filed on Aug. 14, 2008, now Pat. No. 7,853,459.

(51) Int. Cl.
*A61B 5/00* (2006.01)
*G06F 19/00* (2011.01)

(52) U.S. Cl.
USPC ............................................................ 705/3

(58) Field of Classification Search
USPC ...................................................... 705/2, 3
See application file for complete search history.

(56) References Cited

U.S. PATENT DOCUMENTS

| | | |
|---|---|---|
| 5,367,675 A | 11/1994 | Cheng et al. |
| 5,613,072 A | 3/1997 | Hammond et al. |
| 5,911,132 A | 6/1999 | Sloane |
| 6,003,007 A | 12/1999 | DiRienzo |
| 6,049,794 A | 4/2000 | Jacobs et al. |
| 6,108,665 A | 8/2000 | Bair et al. |
| 6,263,330 B1 * | 7/2001 | Bessette ................................ 1/1 |
| 6,434,531 B1 | 8/2002 | Lancelot et al. |
| 6,470,319 B1 | 10/2002 | Ryan |
| 6,581,038 B1 | 6/2003 | Mahran |
| 6,604,080 B1 | 8/2003 | Kern |
| 6,738,784 B1 | 5/2004 | Howes |
| 6,988,088 B1 | 1/2006 | Miikkulainen et al. |
| 7,191,451 B2 | 3/2007 | Nakagawa |
| 7,260,480 B1 | 8/2007 | Brown et al. |
| 2001/0041992 A1 | 11/2001 | Lewis et al. |
| 2001/0044735 A1 | 11/2001 | Colburn et al. |
| 2002/0035486 A1 | 3/2002 | Huyn et al. |
| 2002/0046199 A1 | 4/2002 | Scarborough et al. |

(Continued)

*Primary Examiner* — John Pauls
*Assistant Examiner* — Trang Nguyen
(74) *Attorney, Agent, or Firm* — James W. Hill; Nathan S. Smith; McDermott Will & Emery LLP

(57) ABSTRACT

A machine-implemented method of assisting medical evidence collection for adjudication of a medical disability request is described. In some embodiments, the method includes providing an electronic medical record of a patient, the electronic medical record includes evidence of at least one claimable medical disability condition and locating in the electronic medical record at least one keyword associated with the at least one claimable medical disability condition. In some embodiments, the method further includes processing an inference rule associated with the at least one claimable medical disability condition, such that the evidence of the at least one claimable medical disability condition is identified in the electronic medical record and outputting, to a computer-readable medium, information indicative of (1) the evidence of the at least one claimable medical disability condition, and (2) a location of the evidence in the electronic medical record.

23 Claims, 8 Drawing Sheets

(56) References Cited

U.S. PATENT DOCUMENTS

| | | |
|---|---|---|
| 2002/0046346 A1 | 4/2002 | Evans |
| 2002/0069089 A1 | 6/2002 | Larkin et al. |
| 2002/0091550 A1 | 7/2002 | White et al. |
| 2002/0138306 A1 | 9/2002 | Sabovich |
| 2003/0200123 A1 | 10/2003 | Burge et al. |
| 2004/0006389 A1 | 1/2004 | Steenlage |
| 2004/0030584 A1 | 2/2004 | Harris |
| 2004/0122704 A1* | 6/2004 | Sabol et al. ............ 705/2 |
| 2004/0122705 A1 | 6/2004 | Sabol et al. |
| 2004/0122707 A1 | 6/2004 | Sabol et al. |
| 2004/0122708 A1 | 6/2004 | Avanish et al. |
| 2004/0141661 A1 | 7/2004 | Hanna et al. |
| 2005/0033773 A1 | 2/2005 | Roberge et al. |
| 2005/0131737 A1 | 6/2005 | Joseph et al. |
| 2005/0222867 A1* | 10/2005 | Underwood et al. ............ 705/2 |
| 2005/0256744 A1 | 11/2005 | Rohde et al. |
| 2006/0161463 A1 | 7/2006 | Poomnen et al. |
| 2007/0219829 A1* | 9/2007 | Kay ............................ 705/3 |
| 2009/0192827 A1* | 7/2009 | Andersen et al. ............. 705/4 |

* cited by examiner

| RULEID | RULEID OPERATOR | REQUIREMENT | REQUIREMENT OPERATOR | CATEGORY | CATEGORY KEYWORD | RATING CODE |
|---|---|---|---|---|---|---|
| 1 | AND | 1. IMPAIRED FASTING GLUCOSE<br>2. IFG | OR | DIAGNOSIS | DIABETES | 7913 |
| | | 1. > 100 MG/DL<br>2. < 125 MG/DL | AND | | | |
| 2 | AND | 1. IMPAIRED GLUCOSE TOLERANCE<br>2. IGT | OR | DIAGNOSIS | DIABETES | 7913 |
| | | 1. > 140 MG/DL<br>2. < 199 MG/DL | AND | | | |
| 3 | WITHIN 5 | 1. PLASMA GLUCOSE | (N/A) | DIAGNOSIS | DIABETES | 7913 |
| | | 1. > 199 MG/DL | (N/A) | | | |

| CLAIMED CONDITION | | | | |
|---|---|---|---|---|
| CATEGORY | KEYWORD | PAGE NUMBER | SECONDARY CONDITION | RATING CODE |
| DIAGNOSIS | | | | |
| SECONDARY CONDITION | | | | |
| SYMPTOMATOLOGY | | | | |
| TREATMENT | | | | |
| DIAGNOSTIC TESTS | | | | |

FIG. 5B

| CLAIMED CONDITION | DIABETES MELLITUS 501 | | | |
|---|---|---|---|---|
| CATEGORY 504 | KEYWORD | PAGE NUMBER | SECONDARY CONDITION | RATING CODE |
| DIAGNOSIS | DIABETES | 1,2,9 | | 7913 |
| SECONDARY CONDITION | VISION LOSS | 3  502 | DIABETIC RETINOPATHY | 6068 |
| SYMPTOMATOLOGY | KETOACIDOSIS | 5 | | 7913 |
| TREATMENT | ANTIBIOTIC THERAPY | 7 | 503 | 7913 |
| DIAGNOSTIC TESTS | IMPAIRED FASTING GLUCOSE | 8 | | |

V7-MD Atypical Antipsychotics:
  Atypical Antipsychotic Screening:

CURRENT VITAL MEASUREMENTS:
    Measurement DT    BP

06/15/2007 11:33  144/92
    03/30/2007 14:51  138/91
    03/26/2007 10:58  126/87

BODY MASS INDEX
    JUN 15, 2007@11:33:09   34.0
    MAR 26, 2007@10:58:19   33.0
    FEB 27, 2007@09:15      31.9

SLT - LR ANCILLARY GLUCOSE X 3
    Collection DT     Specimen    Test Name           Result    Units
    Ref Range
    03/30/2007 10:5   PLASMA      GLUCOSE             220 H     mg/dL
    70 - 110
    01/30/2007 14:27  PLASMA      GLUCOSE             123 H     mg/dL
    70 - 110
    11/20/2006 12:36  PLASMA      GLUCOSE             111 H     mg/dL
    70 - 110

MOST RECENT METABOLIC LAB VALUES:
    Collection DT     Spec   CHOL    TRIGLYC  LDL-CHO  LDL/HDL  VLDL  CH
    DIR HDL
       03/30/2007 10:57  PLASM   181    354 H    83.2     3.1 H    70.8 H
    27 L
       01/30/2007 14:27  PLASM   246 H  144      179.2 H  4.7 H    28.8
    38 L Collection DT       Spec  GLUCOSE
       03/30/2007 10:57  PLASM  220 H Collection DT       Spec  A1C
       03/30/2007 10:57  SUPER  6.5 H
       01/30/2007 14:27  SUPER  6.5 H
  Patient is on a new or changed atypical antipsychotic medication and
     requires quarterly monitoring. Monitoring parameters were
     reviewed.
    Fasting lab orders entered for this patient.
      Fasting Lipid Panel ordered.
      HbA1C ordered.
V7-Pneumococcal Vaccine:
  PNEUMOCOCCAL IMMUNIZATION
    Pneumovax was received previously at this or another facility.
      Date: January, 2007

*FIG. 6A*

C&P Final Report                                                      Page: 3

For DIABETES MELLITUS Exam
═══════════════════════════════════════════════════════════════════════════

Exam Results Continued his BG
    this morning was 170. He has a lot of stress because his wife has cancer.

PE: Normal PP and Vibration UE and LE. DTRs 2+.

IMP: Diabetes is out of control. He is setup for diabetic peripheral
    neuropathy. I will check fasting b12 and folate.

Plan: 1. Fasting b12 and folate April 4. 2. He needs better control of
    his diabetes. 3. RTC 3 months.

Staff Neurology
    Signed: 03/31/2006

MEDICAL HISTORY
═══════════════                                            ─── 502

HISTORY OF PANCREATIC TRAUMA:    No

HISTORY OF PANCREATIC NEOPLASM:   No

REPORTED EPISODES OF HYPOGLYCEMIC REACTIONS OR (KETOACIDOSIS):   Yes
    DID ANY OF THESE DIABETIC COMPLICATIONS REQUIRE HOSPITALIZATION:   No

WAS VETERAN INSTRUCTED TO FOLLOW RESTRICTED OR SPECIAL DIET:   Yes

IS VETERAN RESTRICTED IN STRENUOUS ACTIVITES:   No

SYMPTOMS OF DIABETIC RELATED PERIPHERAL VASCULAR DISEASE IN THE LOWER
EXTREMITIES:   No

ARE THERE CARDIAC SYMPTOMS RELATED TO DIABETES:   No

ARE THERE NEUROVASCULAR SYMPTOMS RELATED TO DIABETES:   No

ARE THERE SYMPTOMS OF PERIPHERAL NEUROPATHY RELATED TO DIABETES:   Yes
    DIABETIC RELATED PERIPHERAL NEUROPATHIC SYMPTOM(S):
        Paresthesias
        ANATOMIC LOCATIONS OF ALL PERIPHERAL NEUROPATHIC SYMPTOMS:
            intermittent burning sensation to both arms and hands. He has
            intermittent cramping and spasm to the left forearm and cramp to
            the fourth digit.
            He denies any peripheral neuropathy to the lower extremities.

FIG. 6B

```
MRX:    OD: pl  sph 20/20
        OS: pl  sph 20/20
        ADD: +2.50      20/20 OU SLIT LAMP EXAM
    LLL: normal OD, Papilloma 2x2 ULL
    CONJ: clear OU
    SCLERA: white OU
    K: clear OU
    AC: D/Q OU
    ANGLES: 3x3 OU
    IRIS: normal OU
    LENS: Trace NS OU TAG:    OD:19   OS: 20  @ 8:15am Dilated c 2 gtt of Mydriacil 1% OU @

DILATED FUNDUS EXAM

C/D: .4H/.4V OD, .4H/.4V OS; healthy rim tissue 360 OU
    MAC: +FR OU normal OU
    BCKGRND: normal OU
    VESSELS: 2/3 A/V, 1/3 ALR OU
    PERIPH: normal OU ASSESSMENTS/PLANS
1.  IDDM s retinopathy OU MONITOR at annual exam
2.  HTN s retinopathy OU Monitor at annual exam
3.  Cats  trace NS OU monitor
3.  Presbyopia OU new srx for NVO MONITOR.

,performed a basic exam, I repeated the exam and recorded
the above findings, assessment, and plan.

503
Signed: 12/09/2005

- - - - - - - - - - - - - - - - - - - - - - - - - - - - - - - - - - - - - - - - - -
    LOCAL TITLE: OPTOMETRY CONSULT
STANDARD TITLE: OPTOMETRY CONSULT
DATE OF NOTE: NOV 22, 2005@11:22       ENTRY DATE: NOV 22, 2005@11:22:29
       AUTHOR:                         EXP COSIGNER:
  INSTITUTION: MEMPHIS SOUTH CLINIC (CBOC)
     DIVISION: MEMPHIS SOUTH CLINIC (CBOC)
      URGENCY:                                    STATUS: COMPLETED

Non-mydriatic retinal photographs taken by technician for evaluation of
diabetic
retinopathy.  N( diabetic retinopathy )oted by this examiner.
```

*FIG. 6C*

AUTOMATED PROCESSING OF ELECTRONIC MEDICAL DATA FOR INSURANCE AND DISABILITY DETERMINATIONS

REFERENCE TO RELATED APPLICATIONS

The present application is a continuation of and claims priority benefit under 35 U.S.C. §120 from U.S. patent application Ser. No. 12/192,043, filed Aug. 14, 2008, which is hereby incorporated herein by reference in its entirety.

BACKGROUND OF THE INVENTION

1. Field of the Invention

Some embodiments of the present invention relates to methods and systems for gathering and processing medical data to support rating decisions in the adjudication of insurance and disability requests.

2. Description of the Related Art

Government agencies and insurance companies have developed rules for the adjudication of insurance or disability requests. Examples of insurance or disability programs include the Department of Veterans Affairs (VA) program, the Social Security Disability Insurance program, the Workers' Compensation program, various property and casualty insurance programs, and so forth.

In order to adjudicate a request made by a claimant, certain medical evidence is required. Medical evidence requirements refers to requirements of information about a claimant that is relevant to the medical conditions claimed by the claimant, such as the age and gender of the claimant, physical examination data, laboratory test data and medical history data pertinent to the claims, and so forth. The requirements are specified by rules developed by the government agency or by the insurance company, pertinent case law, government regulations, legislation and administrative decisions, and so forth. For example, the requirements may specify that if a claimant claims a certain medical condition, a medical provider must conduct certain physical examinations and laboratory tests on the claimant or ask certain questions. The requirements may also specify, for example, that a claimant must have a range of motions less than a certain degree to claim a limb disability. Requirements can also be specified by conventional medical knowledge, for example requiring a certain test to confirm a particular claimed condition.

The rating rules are normally documented in manuals that may have many different titles, herein referred to as "rating books." A rating code refers to a classification used by the government agency or insurance company that typically refers to a medical condition or a class of medical conditions in a rating book. The collection of rating rules, rating codes, pertinent legislation and case law for an insurance or disability program is herein referred to as the "rules collection" for that program. The rating rules may include rules on how to make a rating decision based on the collected medical evidence and the rating codes. For example, in a VA disability program, the rules collection typically specifies a disability percentage range based on rating codes and collected medical evidence. A VA rating personnel reviews the rating codes and medical evidence, and specifies a disability percentage within the range.

In a disability or insurance request process, the claimant typically visits a hospital, clinic or medical office. A medical provider such as a physician or a nurse collects medical evidence from the claimant to support a rating decision. The rating decision is typically made by the government agency or the insurance company based on the medical evidence collected by the medical provider and based on the rules collection. The medical providers are typically provided with documents generally referred to as "physician's disability evaluation" or "medical examination handbooks" to assist them with collecting medical evidence. The handbooks are herein referred to as "medical handbooks." The medical handbooks typically contain the medical evidence requirements for the rules collection.

In many cases, a claimant makes claims for multiple medical conditions at different points in time. The conventional practice is to review a medical evidence document each time a condition is claimed. This results in significant duplication of effort as the analysis of portions of the medical evidence document might be conducted multiple times.

To better illustrate the drawbacks of conventional practices and the need for better systems, the VA Compensation and Pension (C&P) program is described as an example. This government program provides payments of benefits to military veterans for medical disability resulting from their military service. Multiple paper records form the basis for the analysis and adjudication of C&P claims for veterans and transitioning active duty service member. In certain cases, sixty percent of all claims are reopened claims and require the paper record to be completely re-reviewed.

SUMMARY

A system is disclosed for automatically relating rating requirements and other pertinent findings from a medical record to a claimed or potentially claimable condition.

In some embodiments, a machine-implemented method of assisting medical evidence collection for adjudication of a medical disability request is disclosed. The method includes providing an electronic medical record of a patient, the electronic medical record includes evidence of at least one claimable medical disability condition and locating in the electronic medical record at least one keyword associated with the at least one claimable medical disability condition. The method further includes processing an inference rule associated with the at least one claimable medical disability condition, such that the evidence of the at least one claimable medical disability condition is identified in the electronic medical record and outputting, to a computer-readable medium, information indicative of (1) the evidence of the at least one claimable medical disability condition, and (2) a location of the evidence in the electronic medical record. The processing an inference rule includes locating an indicator of a value in the electronic medical record that tends to confirm an existence of the claimable medical disability condition in the patient.

In some embodiments, the inference rule is processed if the at least one keyword is present in the electronic medical record. In some embodiments, the method further includes indexing the electronic medical record prior to the locating in the electronic medical record the at least one keyword. In some embodiments, the at least one keyword is selected from a plurality of keywords associated with the at least one claimable medical disability condition. In some embodiments, the method further includes determining, for each of the plurality of keywords, whether that keyword is included in the electronic medical record. In some embodiments, the inference rule includes searching, in the electronic medical record, for information associated with the at least one keyword. In some embodiments, the inference rule utilizes at least one of information on a category associated with the at least one keyword, a rating code, and a search query. In some embodiments, the information indicative of the evidence of the at least one claimable medical disability condition includes at least one of a secondary condition associated with the at least one claimable medical disability condition, a category associated with the at least one claimable medical disability condition, and a rating code associated with the at least one claimable medical disability condition.

In some embodiments, a machine-implemented method of assisting medical evidence collection for adjudication of a medical disability request is disclosed. The method includes providing an electronic medical record of a patient, the electronic medical record includes evidence of at least one claimable medical disability condition and processing an inference rule associated with the at least one claimable medical disability condition, such that the evidence of the at least one claimable medical disability condition is identified in the electronic medical record. The method also includes outputting, to a computer-readable medium, information indicative of (1) the evidence of the at least one claimable medical disability condition, and (2) a location of the evidence in the electronic medical record. The processing an inference rule includes locating an indicator of a value in the electronic medical record that tends to confirm an existence of the claimable medical disability condition in the patient.

In some embodiments, a machine-readable medium encoded with instructions for assisting medical evidence collection for adjudication of a medical disability request is disclosed. The instructions include code for locating in an electronic medical record at least one keyword associated with at least one claimable medical disability condition and processing an inference rule associated with the at least one claimable medical disability condition, such that the evidence of the at least one claimable medical disability condition is identified in the electronic medical record. The instructions also include code for outputting, to a computer-readable medium, information indicative of (1) the evidence of the at least one claimable medical disability condition, and (2) a location of the evidence in the electronic medical record. The processing an inference rule includes locating an indicator of a value in the electronic medical record that tends to confirm an existence of the claimable medical disability condition in the patient.

In some embodiments, a machine-readable medium encoded with instructions for assisting medical evidence collection for adjudication of a medical disability request is disclosed. The instructions include code for processing an inference rule associated with at least one claimable medical disability condition, such that evidence of the at least one claimable medical disability condition is identified in the electronic medical record, and outputting, to a computer-readable medium, information indicative of (1) the evidence of the at least one claimable medical disability condition, and (2) a location of the evidence in the electronic medical record. The processing an inference rule includes locating an indicator of a value in the electronic medical record that tends to confirm an existence of the claimable medical disability condition in the patient.

In some embodiments, a system, for assisting medical evidence collection for adjudication of a medical disability request, is disclosed. The system includes a searching module configured to locate in an electronic medical record at least one keyword associated with at least one claimable medical disability condition and a processing module configured to process an inference rule associated with the at least one claimable medical disability condition, such that the evidence of the at least one claimable medical disability condition is identified in the electronic medical record, the processing module further configured to send an output to an output module. The output includes computer-readable information indicative of (1) the evidence of the at least one claimable medical disability condition, and (2) a location of the evidence in the electronic medical record. The processing an inference rule includes locating an indicator of a value in the electronic medical record that tends to confirm an existence of the claimable medical disability condition in the patient.

In some embodiments, a system, for assisting medical evidence collection for adjudication of a medical disability request, is disclosed. The system includes a processing module configured to process an inference rule associated with at least one claimable medical disability condition, such that the evidence of at least one claimable medical disability condition is identified in an electronic medical record, the processing module further configured to send an output to an output module. The output includes computer-readable information indicative of (1) the evidence of the at least one claimable medical disability condition, and (2) a location of the evidence in the electronic medical record. The processing an inference rule includes locating an indicator of a value in the electronic medical record that tends to confirm an existence of the claimable medical disability condition in the patient.

In some embodiments, a system, for assisting medical evidence collection for adjudication of a medical disability request, is disclosed. The system includes means for providing an electronic medical record of a patient, the electronic medical record includes evidence of at least one claimable medical disability condition, and means for locating in the electronic medical record at least one keyword associated with the at least one claimable medical disability condition. The system also includes means for processing an inference rule associated with the at least one claimable medical disability condition, such that the evidence of the at least one claimable medical disability condition is identified in the electronic medical record, and means for outputting, to a computer-readable medium, information indicative of (1) the evidence of the at least one claimable medical disability condition, and (2) a location of the evidence in the electronic medical record. The processing an inference rule includes locating an indicator of a value in the electronic medical record that tends to confirm an existence of the claimable medical disability condition in the patient.

In some embodiments, a system, for assisting medical evidence collection for adjudication of a medical disability request, is disclosed. The system includes means for providing an electronic medical record of a patient, the electronic medical record includes evidence of at least one claimable medical disability condition, and means for processing an inference rule associated with the at least one claimable medical disability condition, such that the evidence of the at least one claimable medical disability condition is identified in the electronic medical record. The system also includes means for outputting, to a computer-readable medium, information indicative of (1) the evidence of the at least one claimable medical disability condition, and (2) a location of the evidence in the electronic medical record. The processing an inference rule includes locating an indicator of a value in the electronic medical record that tends to confirm an existence of the claimable medical disability condition in the patient.

In some embodiments, processing an inference rule consists essentially of locating in the electronic medical record at least one keyword associated with the at least one claimable medical disability condition.

For purposes of summarizing the invention, certain aspects, advantages, and novel features of the invention have been described herein. It is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

BRIEF DESCRIPTION OF THE DRAWINGS

A general architecture that implements the various features of the invention will now be described with reference to the drawings. The drawings and the associated descriptions are provided to illustrate embodiments of the invention and not to limit the scope of the invention. Throughout the drawings, reference numbers are re-used to indicate correspondence between referenced elements.

FIG. 2 illustrates sample inference rules associated with a claim condition.

FIGS. 5A-5B illustrate values associated with a sample entry in an evidence repository for an EMR.

FIGS. 6A-6C illustrate pages of a sample EMR.

DETAILED DESCRIPTION OF EXEMPLARY EMBODIMENTS

Figure 1:
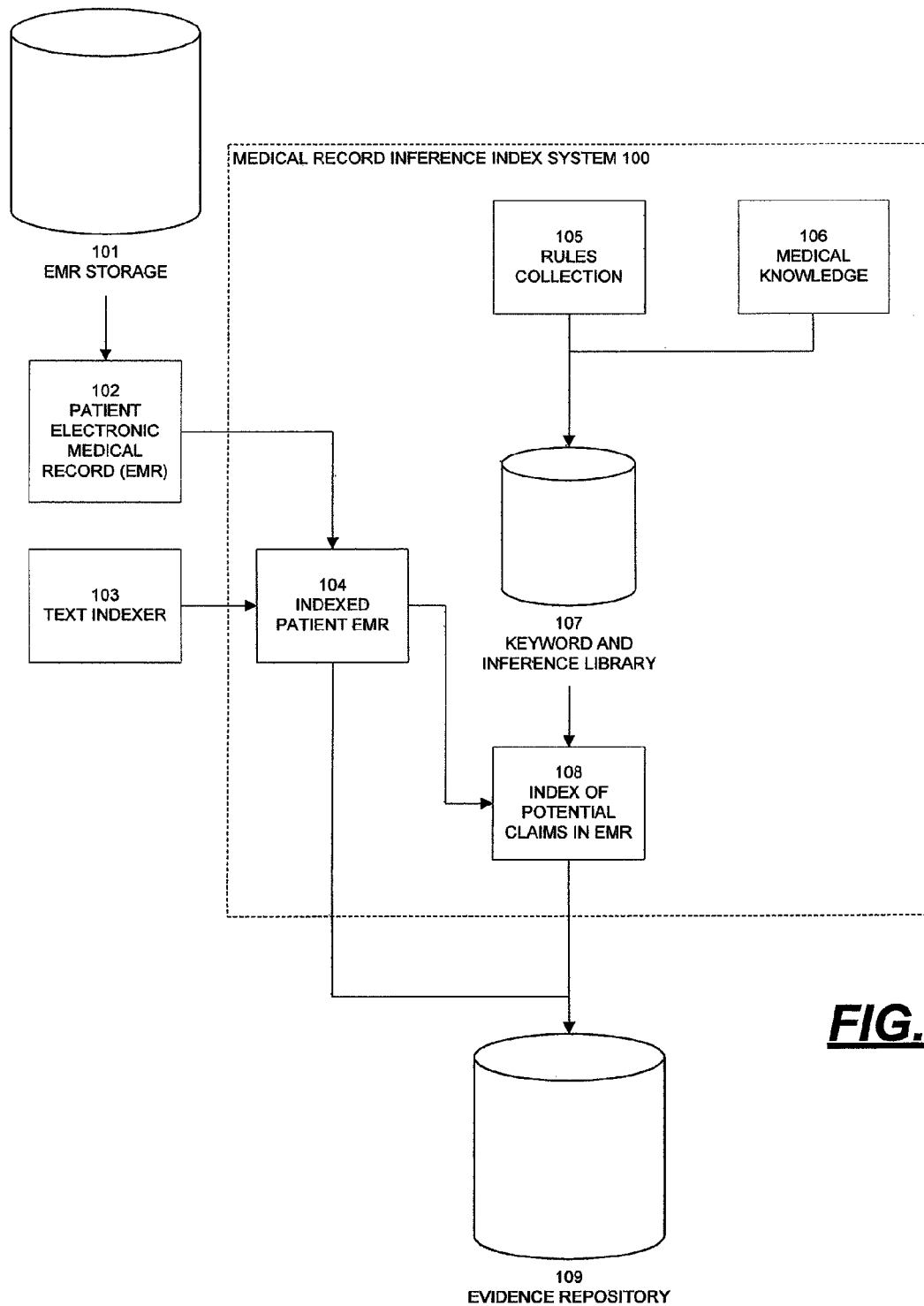
FIG. 1 illustrates a general overview of one embodiment of a medical record inference index system.

FIG. 1 illustrates a general overview of one embodiment of a medical record inference index system 100. The medical record inference index system 100 includes rules collection 105, pertinent medical knowledge 106, keyword and inference library 107, at least one indexed patient EMR 104, and an index of potential patient claims in the EMR 108.

Rules collection 105 and pertinent medical knowledge 106 are organized into a keyword and inference library 107. Based on an indexed patient EMR 104, which was created by applying text indexer 103 to a patient EMR 102 selected from EMR storage 101, and based on the keywords and inference rules in the keyword and inference library 107, an index of potential claims 108 present in indexed patient EMR 104 is generated. The index of potential claims is stored in evidence repository 109.

EMR storage 101 is electronic data storage configured to store at least one EMR (e.g., EMR 104). As used herein, an electronic medical record includes, without limitation, medical information stored in an electronic format. The medical information can include, for example, notes from a patient's medical history, family and social history, complaints, office visits, staff observations, laboratory tests, X-rays, prescription and drug allergy information, social history, diagnoses, data from charts, radiological study results, nuclear medicine laboratory results, present medication, allergy and chronic condition lists (e.g., from medical alert bracelets), histories of a present illness, a review of systems, physical exams, interviews with friends and family of the claimant, interviews of the claimant's prior medical providers, and other medical records of the patient. For example, an EMR can be an electronic Veteran's Health Administration (VHA) record or a Department of Defense (DoD) record. The electronic data storage may comprise any type of computer-readable media, including hard disk drives, removable magnetic disks, removable optical disks, magnetic cassettes, flash memory cards, digital video disks, Bernoulli cartridges, random access memories, read-only memories, and the like, and may be configured as a file server, database, or other data object. Electronic formats include, but are not limited to, scanned documents, such as scanned paper records, or documents originally generated and subsequently stored electronically, such as text files.

Text indexer 103 is configured to index EMR 102 in order to provide indexed patient EMR 104, an indexed version of EMR 102. As a result, in certain embodiments, indexed information in indexed patient EMR 104 can be located in sublinear, logarithmic, or constant time. In one embodiment, text indexer 103 provides a full-text indexing of EMR 102. In certain embodiments, text indexer 103 includes optical character recognition of content in EMR 102 when indexing EMR 102. Any conventional algorithm known to those of skill in the art may be used to implement text indexer 103.

Still referring to FIG. 1, rule collection 105 represents a rules collection for the insurance or disability program, typically embodied in rating books, legislation, administrative decisions and case law. For example, rule collection 105 can include the "Schedule for Ratings Disabilities" from Title 38 of the Code of Federal Regulations (CFR) (hereinafter "Schedule for Ratings Disabilities"). Medical knowledge 106 represents pertinent medical knowledge, such as instructions to a physician, lab technician or nurse for performing a physical exam or laboratory test, and information from a contractor's extensive disability examination experience and its experience supporting the Veteran's Benefit Administration with C&P examinations.

Keyword and inference library 107 includes claimable medical disability conditions relating to medical disabilities, a collection of keywords associated with the claimable medical disability conditions relating to medical disabilities, and a collection of inference rules associated with the keywords. According to certain embodiments, keyword and inference library 107 is organized according to the claimable medical disability conditions. A keyword as discussed herein includes, without limitation, either a single or multiple letters, words, acronyms, abbreviations, or numerals. For example, "diabetes mellitus," "insulin dependent diabetes," "adult onset diabetes," "insulin dependent diabetes mellitus," "IDDM," "vision loss," "nephropathy," "amputation," "renal failure," "diabetic ketoacidosis," "antibiotic therapy," "impaired fasting glucose," and "IFG" may be keywords associated with the claimable medical disability condition of diabetes mellitus.

Inference rules as discussed herein include, without limitation, values and/or parameters to be applied to an EMR (e.g., indexed patient EMR 104) to determine if the EMR satisfies the values and/or contains the values, and actions to be taken if the EMR satisfies the values and/or contains the values. In certain embodiments, the actions include assigning a rating code based on available rating books, such as the Schedule for Ratings Disabilities. In certain embodiments, inference rules may be associated with additional claim conditions, such as related claim conditions. For example, inference rules that assist in locating evidence of diabetes mellitus may also assist in locating evidence of heart disease.

For example, FIG. 2 illustrates sample inference rules associated with the claimable medical disability condition of diabetes mellitus. The sample inference rules include an inference rule 201, with a "RULEID" value of 3. Inference rule 201, if processed on an EMR, determines that if the EMR contains the string "plasma glucose" within five words distance from a value greater than 199 mg/d, then a record (e.g., index of potential claims in EMR 108) is created and stored (e.g., in evidence repository 109) in which (1) the EMR (e.g., EMR 102 or indexed patient EMR 104) is identified as containing evidence of the claimable medical disability condition with which the inference rule is associated, diabetes mellitus, (2) the page number containing the subject matter satisfying the inference rule is stored, (3) the category "diagnosis" is set to "diabetes," and (4) the rating code is assigned a value of "7913," which is the rating code for diabetes in the Schedule for Ratings Disabilities. The record can be supplemented with additional information on the same or different claimable medical disability conditions that are found in the same EMR using other inference rules. In certain embodiments, relevant portions of the EMR may be tagged in order to facilitate referencing of the EMR, such as by tagging a portion of the EMR identified as containing evidence of the claimable medical disability condition with which the inference rule is associated. Additional records can also be created and stored in evidence repository 109, which may also be electronic storage, for other EMRs. For example, in an object-oriented arrangement, a claimable medical disability condition can be associated with an object that includes various fields for "RULEID,""RULEID OPERATOR," "REQUIREMENT, ""REQUIREMENT OPERATOR,""CATEGORY,""CATEGORY KEYWORD," and "RATING CODE."

In certain embodiments, inference rules are generated based on the units of data that may be required by rules collection 105 for assigning a rating code. For example, an inference rule can correspond to a medical evidence requirement specified by rules collection 105 or by medical knowledge 106.

A collection of potential claimable medical disability conditions found in an EMR for a patient can thus be generated and stored, and later reviewed to assist a physician, rating specialist, nurse or technician to confirm actual claimable medical disability conditions for the patient. Furthermore, the collection can be recalled and re-reviewed at any time without having to retrieve voluminous paper or electronic files. For example, if an EMR for a patient is reviewed by the medical record inference index system 100 a first time, and after the first review the EMR is supplemented with additional information, the medical record inference index system 100 may highlight or otherwise differentiate new information during a second review that was not present during the first review. In certain embodiments, the medical record inference index system 100 is configured to differentiate between actual claimed conditions by a patient and potentially claimable conditions by a patient.

Figure 3:
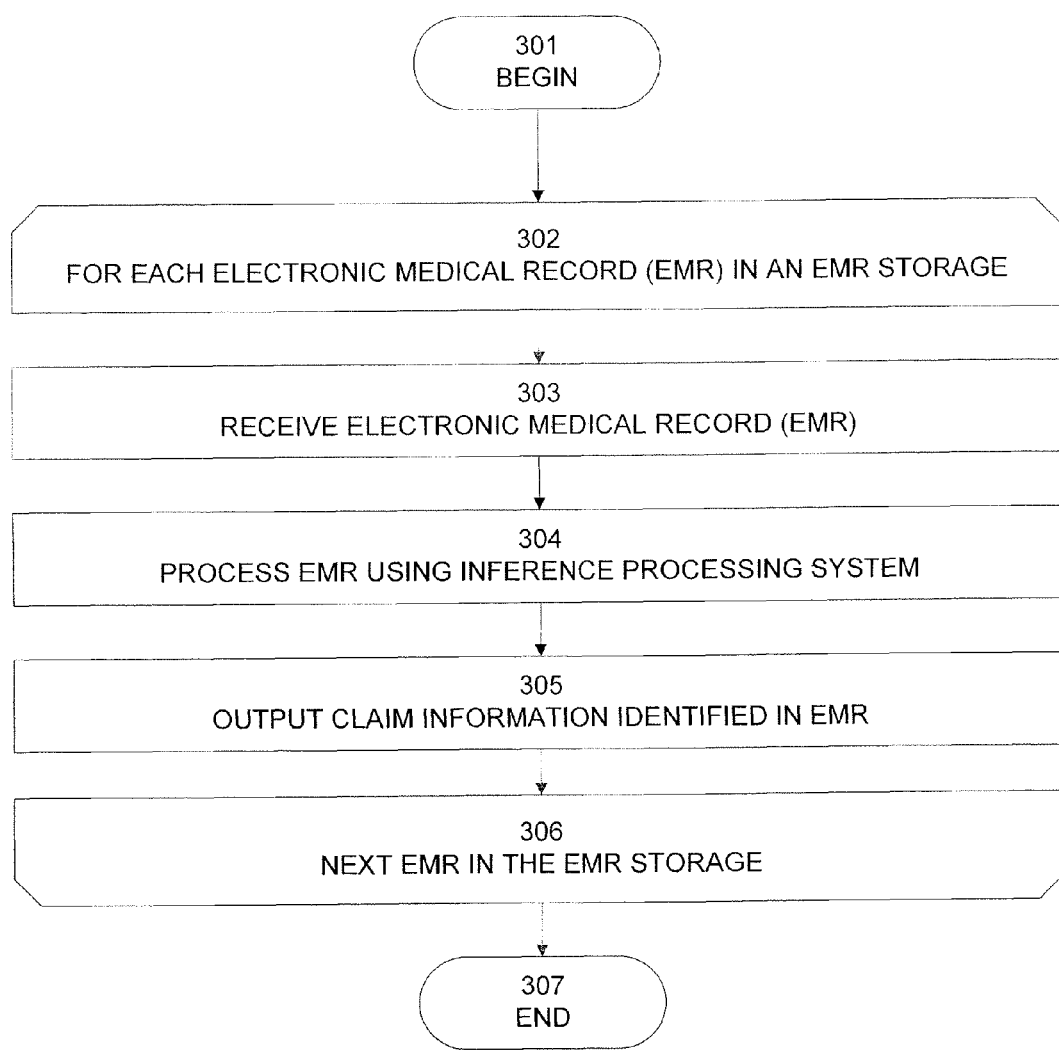
FIG. 3 is one embodiment of a process for identifying disability benefits claims.

In certain embodiments, claimable medical disability conditions and associated information can be specific to the claimant or specific to the type of claim. For example, information associated with a claimable medical disability condition can be associated with information relevant or specific to the claimant (e.g., claimed medical conditions, name, age, gender) and/or to the type of claim (e.g., leg pain, chest pain, head pain). Examples of claim-specific, claimant-specific, and claim-type specific information can be found in U.S. patent application Ser. No. 10/279,759, filed Oct. 23, 2002, U.S. patent application Ser. No. 11/155,908, filed Jun. 20, 2005, and U.S. patent application Ser. No. 11/157,125, filed on Jun. 20, 2005, each of which is hereby incorporated herein by reference in its entirety FIG. 3 is one embodiment of a process for identifying disability benefits claims. The process begins in step 301, and proceeds to step 302, in which a loop is entered for each EMR 102 in EMR storage 101. In the first step of the loop, step 303, EMR 102 is received. For example, EMR 102 may be actively retrieved by a module, or received from another module that sends EMR 102. EMR 102 is processed in step 304 using the medical record inference index system 100 of FIG. 1, as further described in FIG. 4. Claim information identified in EMR 102 is output to an output device in step 305, such as by printing a record of claimable medical disability conditions found in EMR 102. Output devices may include but are not limited to, a display monitor, a printer, paper, the human voice, computer memory, volatile (such as RAM) or non-volatile (such as a hard disk drive), an electronically generated voice, and output computer languages, specifications, or formats such as the Extensible Markup Language (XML) or Comma Separated Values (CSV) format, or standards such as Health Level Seven (HL7). The process then moves to end-of-loop step 306, in which another EMR in EMR storage 101 is retrieved, and steps 203-205 are repeated for the EMR. If no EMR remains in EMR storage 101 in step 306, the process ends in step 307. In certain embodiments, the identified claim information output in step 305 can be reviewed by a human reviewer to ensure the accuracy of the information.

Figure 4:
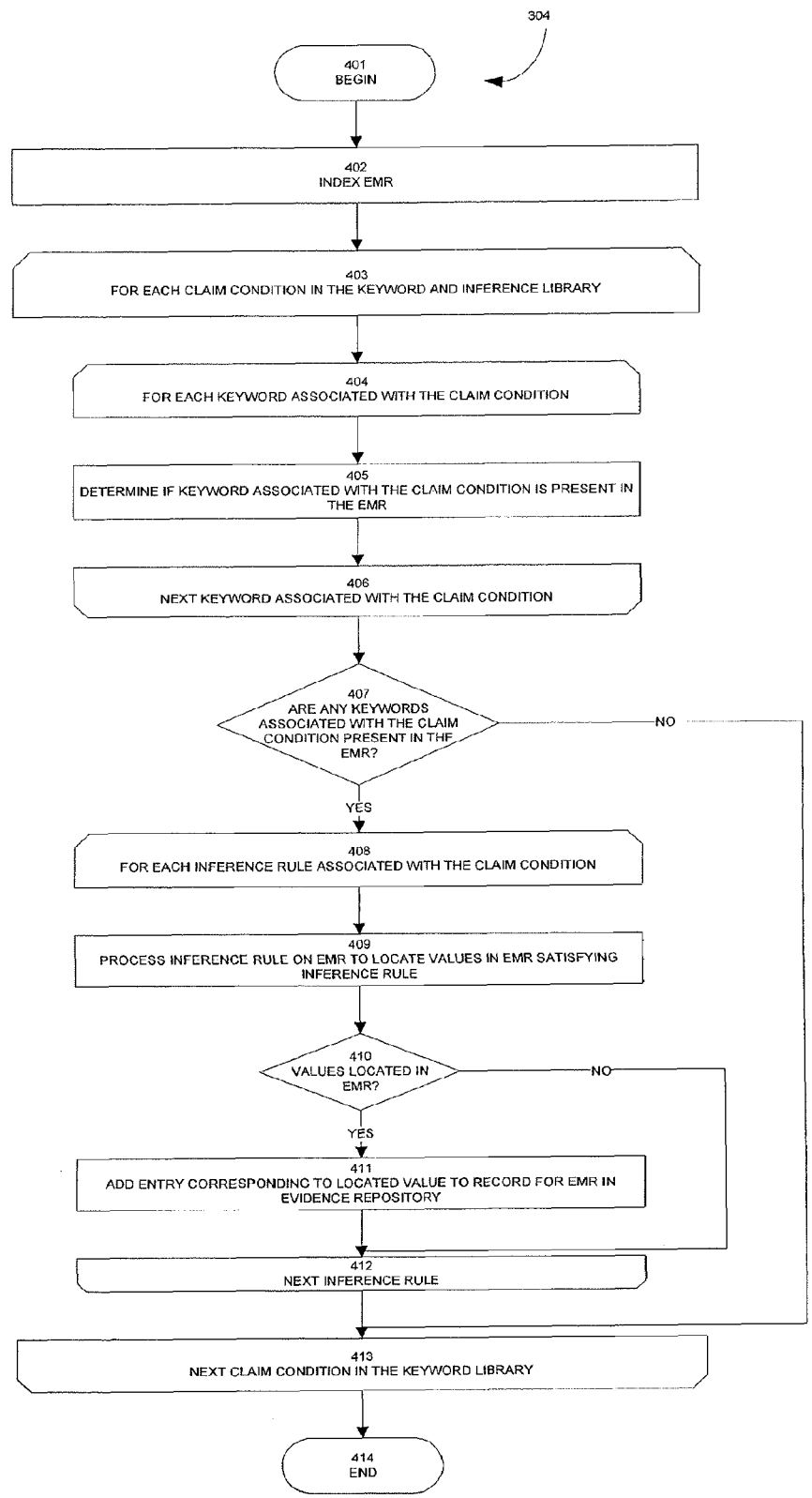
FIG. 4 is one embodiment of processing an electronic medical record (EMR) using the medical record inference index system of FIG. 1.

FIG. 4 is one embodiment of processing an electronic medical record (EMR) using the medical record inference index system of FIG. 1, and provides further elaboration for step 304 of FIG. 3.

The process begins in step 401, and proceeds to step 402, in which the EMR (e.g., EMR 102) is optionally indexed, to generate the indexed EMR (e.g., indexed EMR 104). For example, in addition to word-indexing the EMR, as described above, the EMR may be indexed by patient name, page, date, location, physician, record type, page number, case related information such as claim number or claim conditions. In certain embodiments, the EMR is already indexed, and step 402 is skipped. In certain embodiments, the EMR does not need to be indexed to proceed with the process, and the system 100 is configured to provide an index of potential claims from a non-indexed EMR.

In step 403, a loop is entered for each claim condition in a keyword and inference library (e.g., keyword and inference library 107). A sub-loop is further entered in step 404 for each keyword associated with each claim condition. In the sub-loop, which proceeds to step 405, the indexed EMR is processed to determine whether the keyword of step 403 is present in the indexed EMR. The process proceeds to step 406, in which the sub-loop is repeated for each keyword associated with the claim condition. In certain embodiments (not illustrated), the sub-loop of steps 404-406 may end when any keyword associated with the claim condition is determined to be present in the indexed EMR.

In step 407, if any keywords associated with the claim condition were determined to be present in the indexed EMR during the sub-loop of steps 404-406, then the process proceeds to step 408. If no keywords associated with the claim condition were determined to be present in the indexed EMR, then the process proceeds to step 413, in which the loop of step 403 either returns to step 403 if another claim condition remains in the keyword and inference library, or ends in state 414 if no claim conditions remain in the keyword and inference library.

In step 408, i.e., if a keyword associated with the claim condition is present in the indexed EMR, then steps 409-411 are repeated for each inference rule associated with the claim condition. In step 409, the inference rule is processed on the indexed EMR to locate values (or indicators of values) in the indexed EMR satisfying the inference rule. The values can include, without limitation, numeric values, such as a value of 130 indicating a blood sugar level, binary values, such as a yes or no value indicating a history of cancer, character values, string values, or other values.

In decision step 410, if such values are located in the indexed EMR, then the process proceeds to step 411. If, however, in decision step 410, if such values are not located in the indexed EMR, then the process proceeds to end-of-loop step 412.

In step 411, an entry corresponding to the located value is added to a record (e.g., index of potential claims in EMR 108) associated with the indexed EMR stored in an evidence repository (e.g., evidence repository 109). In step 412, if any inference rules remain which are associated with the claim condition of step 403, then the process returns to beginning-of-loop step 408. Otherwise, if no inference rules remain which are associated with the claim condition of step 403, then the process proceeds to step 413.

In step 413, if any claim conditions remain in the keyword and inference library, then the process returns to beginning-of-loop step 403. Otherwise, if no claim conditions remain in the keyword and inference library, then the process ends in step 414.

In certain embodiments, after step 403, steps 404-407 may be skipped, and the process may proceed immediately to step 408. As a result, inference rules associated with each claim condition may be processed on an EMR in order to add entries corresponding to located values to a record for the EMR in the evidence repository.

According to one embodiment, FIGS. 5A-5B illustrate a sample record (e.g., index of potential claims in EMR 108) associated with a sample EMR (e.g., patient the EMR) which includes information on potential claims located in an indexed version of the EMR (e.g., index of potential claims in EMR 108). FIGS. 6A-6C illustrate selected pages from the sample EMR.

FIG. 5A illustrates the sample record before the record has been populated with any information related to the sample EMR. For example, the illustrated sample record may represent a record during steps 401-410 of the process illustrated in FIG. 4. The sample record is configured to store information on a claimed condition, as well as any keywords, page numbers, secondary conditions, and rating codes associated with a diagnosis, secondary condition, symptomatology, treatment, and diagnostic test(s) of the claimed condition. In certain embodiments, a record can be configured to store other information.

FIG. 5B illustrates the sample record of FIG. 5A after inference processing has occurred. For example, the sample record may represent a record after at least step 411 of the process illustrated in FIG. 4 is processed on the sample EMR illustrated in FIGS. 6A-6C using the sample inference rule of FIG. 3. Because sample inference rule 201 is satisfied by the sample EMR, i.e., the sample EMR contains the phrase "plasma glucose" within five words distance of a value greater than 199 mg/dl at 201 in FIG. 6A, the "claimed condition" value of the sample record is set to "diabetes mellitus" 501 and the "diagnosis" category of the record is set to "diabetes" 504 with a rating code of 7913 and the appropriate page number, according to the parameters of sample inference rule 201. Likewise, additional inference rules associated with the entries of "ketoacidosis" 502 (the phrase being located at 502 in FIG. 6B) and "diabetic retinopathy" 503 (the phrase being located at 503 in FIG. 6C) are also recorded in the sample record.

The sample record illustrated in FIG. 5A listing potential claims found in an EMR can be displayed after the process of FIG. 3 is complete. For example, the list of potential claims and associated information can be displayed to a medical provider on the screen of an electronic device, and the medical provider can then have easy access to potential claim information for a patient without having to identify or otherwise locate information in the EMR first.

According to one aspect of the disclosure, a machine-readable medium is a computer-readable medium encoded or stored with instructions and is a computing element, which defines structural and functional interrelationships between the instructions and the rest of the system, which permit the instructions' functionality to be realized. Instructions may be executable, for example, by a medical record inference index system or by a processor of a medical record inference index system. Instructions can be, for example, a computer program including code. A machine-readable medium may comprise one or more media.

While certain aspects and embodiments of the invention have been described, these have been presented by way of example only, and are not intended to limit the scope of the invention. Indeed, the novel methods and systems described herein may be embodied in a variety of other forms without departing from the spirit thereof. The accompanying claims and their equivalents are intended to cover such forms or modifications as would fall within the scope and spirit of the invention.

What is claimed is:

1. A system, for assisting medical evidence collection for adjudication of a medical disability request, comprising:
   a computer-readable library storing an inference rule associated with at least one claimable medical disability condition; and
   a processor configured to identify and locate, based on the inference rule, evidence in an electronic medical record of a patient that tends to confirm or disconfirm an existence of the claimable medical disability condition in the patient, and to display a visible association between (1) the identified evidence and (2) a location reference of the identified evidence in the electronic medical record.

2. The system of claim 1, wherein the identified evidence and the location reference of the identified evidence in the electronic medical record are visibly associated in a table.

3. The system of claim 2, wherein the visible association comprises a proximate position, of the identified evidence and the location reference of the identified evidence, within the table.

4. The system of claim 2, wherein the table comprises a value from the electronic medical record that tends to confirm or disconfirm the at least one claimable medical disability condition.

5. The system of claim 2, wherein the visible association comprises displaying the identified evidence and the location reference of the identified evidence in the electronic medical record within a single row of the table.

6. The system of claim 1, wherein the processor is also configured to electronically tag a portion of the electronic medical record that includes the identified evidence.

7. The system of claim 1, wherein the inference rule utilizes at least one of information on a category associated with the identified evidence, a rating code, or a search query.

8. The system of claim 1, wherein the value comprises at least one of a secondary condition associated with the at least one claimable medical disability condition, a category associated with the at least one claimable medical disability condition, or a rating code associated with the at least one claimable medical disability condition.

9. The system of claim 1, wherein the identified evidence confirming or disconfirming the at least one claimable medical disability condition comprises at least one keyword associated with the at least one claimable medical disability condition.

10. The system of claim 9, wherein the at least one keyword is selected from a plurality of keywords associated with the at least one claimable medical disability condition.

11. The system of claim 1, wherein the processor is further configured to display simultaneously a visible association between the (1) the identified evidence, (2) the location reference, and (3) the query regarding the claimable medical disability condition.

12. A method of assisting medical evidence collection for adjudication of a medical disability request, comprising:
   providing an electronic medical record of a patient, the electronic medical record comprising evidence confirming or disconfirming at least one claimable medical disability condition;
   identifying, using a processor, and based on an inference rule associated with the at least one claimable medical disability condition, evidence in the electronic medical record that tends to confirm or disconfirm an existence of, the at least one claimable medical disability condition in the patient; and
   outputting, to a display, a visible association between information indicative of the identified evidence confirming or disconfirming the at least one claimable medical disability condition, (2) a location reference of the identified evidence in the electronic medical record.

13. The method of claim 12, wherein the outputting a visible association between the information indicative of the identified evidence and the location reference of the identified evidence is output in a table.

14. The method of claim 13, wherein the visible association comprises a proximate position, of the information indicative of the identified evidence and the location reference of the identified evidence, within the table.

15. The method of claim 13, wherein the visible association comprises displaying the information indicative of the identified evidence and the location reference of the identified evidence in the electronic medical record within a single row of the table.

16. The method of claim 12, further comprising indexing the electronic medical record prior to the identifying the evidence in the electronic medical record.

17. The method of claim 12, wherein the identified evidence comprises a keyword associated with the at least one claimable medical disability condition.

18. The method of claim 17, wherein the keyword is selected from a plurality of keywords associated with the at least one claimable medical disability condition.

19. The method of claim 12, wherein the inference rule utilizes at least one of information on a category associated with the identified evidence, a rating code, or a search query.

20. The method of claim 12, wherein the evidence confirming or disconfirming the at least one claimable medical disability condition comprises at least one of a secondary condition associated with the at least one claimable medical disability condition, a category associated with the at least one claimable medical disability condition, or a rating code associated with the at least one claimable medical disability condition.

21. The method of claim 12, wherein the outputting further comprises simultaneously outputting to a display a visible association between the (1) the identified evidence, (2) the location reference, and (3) the query regarding the claimable medical disability condition.

22. A non-transitory machine-readable medium encoded with instructions for adjudication of a medical disability request, comprising:
   providing an electronic medical record of a patient, the electronic medical record comprising evidence confirming or disconfirming at least one claimable medical disability condition;
   identifying, using a processor, and based on an inference rule associated with the at least one claimable medical disability condition, evidence in the electronic medical record that tends to confirm or disconfirm an existence of, the at least one claimable medical disability condition in the patient; and
   outputting, to a display, a visual association between information indicative of the identified evidence confirming or disconfirming the at least one claimable medical disability condition, and a location reference of the identified evidence in the electronic medical record.

23. The non-transitory machine-readable medium of claim 22, wherein the outputting further comprises simultaneously outputting to a display a visible association between the (1) the identified evidence, (2) the location reference, and (3) the query regarding the claimable medical disability condition.

* * * * *